United States Patent [19]

Jagger et al.

[11] Patent Number: 4,932,944

[45] Date of Patent: Jun. 12, 1990

[54] INTRAVENOUS PORT INJECTION AND CONNECTOR SYSTEM

[75] Inventors: Janine C. Jagger; Richard D. Pearson; Patrice G. Guyenet, all of Charlottesville, Va.

[73] Assignee: The University of Virginia Alumni Patents Foundation, Charlottesville, Va.

[21] Appl. No.: 166,076

[22] Filed: Mar. 9, 1988

[51] Int. Cl.⁵ .............................................. A61M 5/08
[52] U.S. Cl. .................................... 604/191; 604/192; 604/413; 604/51
[58] Field of Search ............................ 604/86–88, 604/412, 413, 414, 201, 205, 192, 193, 191, 202, 203, 51

[56] References Cited

U.S. PATENT DOCUMENTS

| | | | |
|---|---|---|---|
| 2,939,459 | 6/1960 | Lazarte et al. | 604/191 |
| 3,028,052 | 4/1962 | Archer | 604/88 |
| 3,200,813 | 8/1965 | Christakis | 604/201 |
| 3,368,558 | 2/1968 | Sarnoff et al. | 604/201 |
| 3,382,865 | 5/1968 | Worrall, Jr. | 604/201 |
| 3,826,260 | 7/1974 | Killinger | 604/413 |
| 3,896,805 | 7/1975 | Weingarter | 604/191 |
| 3,911,916 | 10/1975 | Stevens | 604/203 |
| 4,014,330 | 3/1977 | Genese | 604/88 |
| 4,055,177 | 10/1977 | Cohen | 604/88 |
| 4,180,070 | 12/1979 | Genese | 604/88 |
| 4,232,669 | 11/1980 | Nitshke | 604/192 |
| 4,303,069 | 12/1981 | Cohen | 604/192 |
| 4,313,440 | 2/1982 | Ashley | 604/191 |
| 4,439,184 | 3/1984 | Wheeler | 604/191 |
| 4,453,934 | 6/1984 | Gähwiler et al. | 604/191 |
| 4,529,403 | 7/1985 | Kamstra | 604/191 |
| 4,643,721 | 2/1987 | Brunet | 604/191 |
| 4,676,703 | 6/1987 | Jagger et al. | 604/171 |
| 4,702,737 | 10/1987 | Pizzino | 604/191 |
| 4,715,854 | 12/1987 | Vaillancourt | 604/191 |
| 4,759,956 | 7/1977 | Forman et al. | 604/82 |

FOREIGN PATENT DOCUMENTS 2050184 1/1981 United Kingdom.

Primary Examiner—C. Fred Rosenbaum
Assistant Examiner—Kathleen Daley
Attorney, Agent, or Firm—James C. Wray

[57] ABSTRACT

A connector has one end for receiving a standard auxiliary line adaptor hub and an opposite end receivable over an intravenous line port in a male-female interference fit. A needle is provided in the interior of the connector and punctures a sealing membrane provided over the line port. After the needle has been properly positioned in the line port, an external ring is slid axially over the male-female connection to tighten the interference fit.

For a heparin flush, a cylinder has two chambers, one for holding heparin and another for holding saline. The two chambers are separated by a membrane. A rubber stopper is provided at one end of the cylinder and is provided with a screw connector for receiving a plunger. The opposite end is provided with a needle having inner and outer points, the needle being recessed into an end portion of the cylinder.

The outer end of the needle is provided with a sheath which is removed prior to sliding an intravenous line port into the cylinder. Following puncture by the outer point of the needle, the plunger is pushed inwardly to force saline solution from the first chamber through the needle. After expulsion of the contents of the first chamber, the inner point of the needle pierces the membrane separating the first chamber from the second chamber and further inward movement of the plunger expels the contents of the second chamber.

6 Claims, 2 Drawing Sheets

FIG. 1
FIG. 2
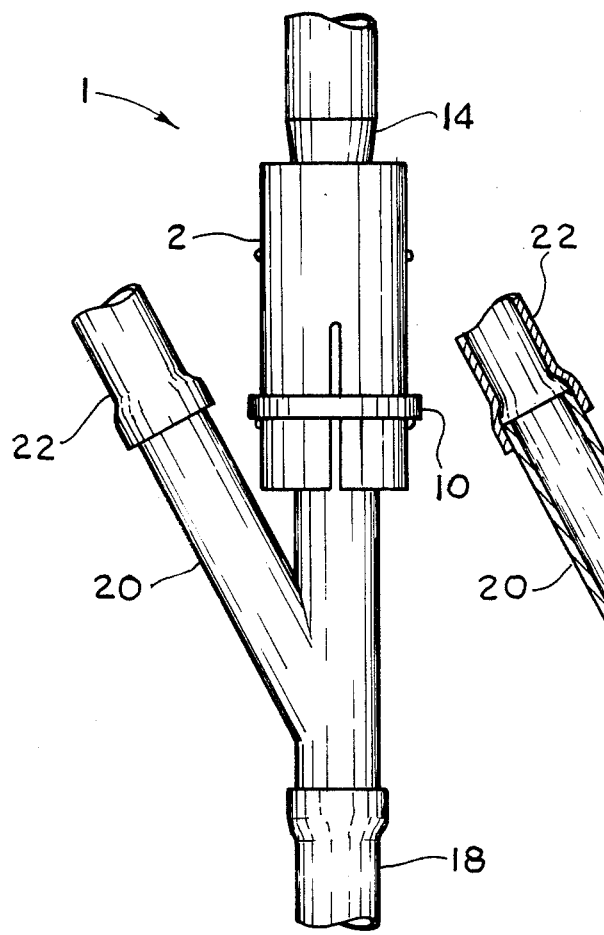
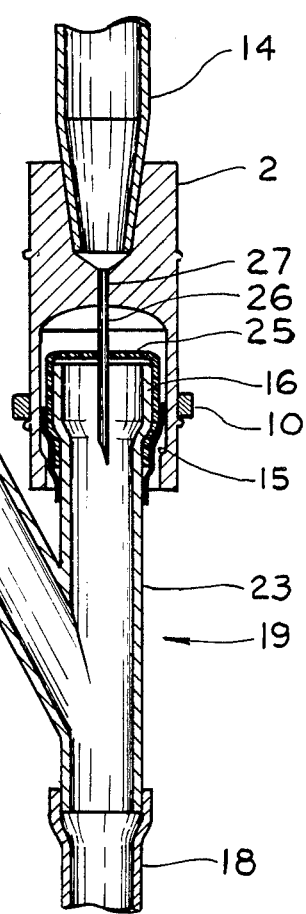
FIG. 1A
FIG. 2A
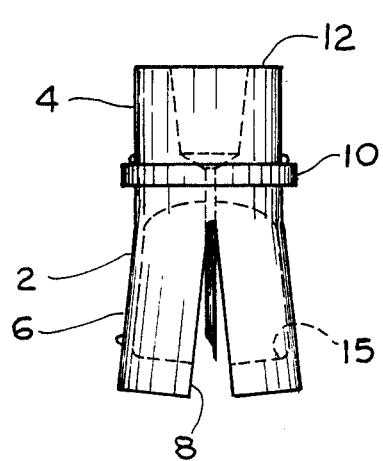
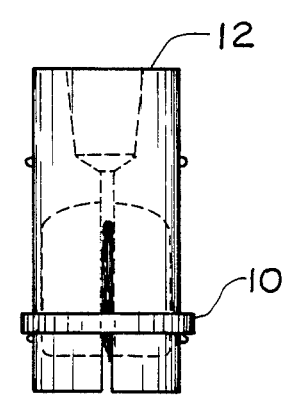

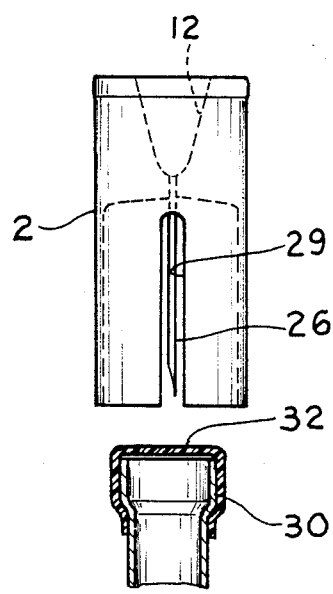
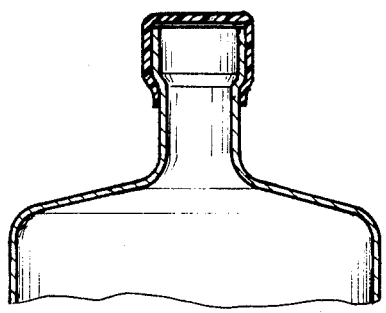
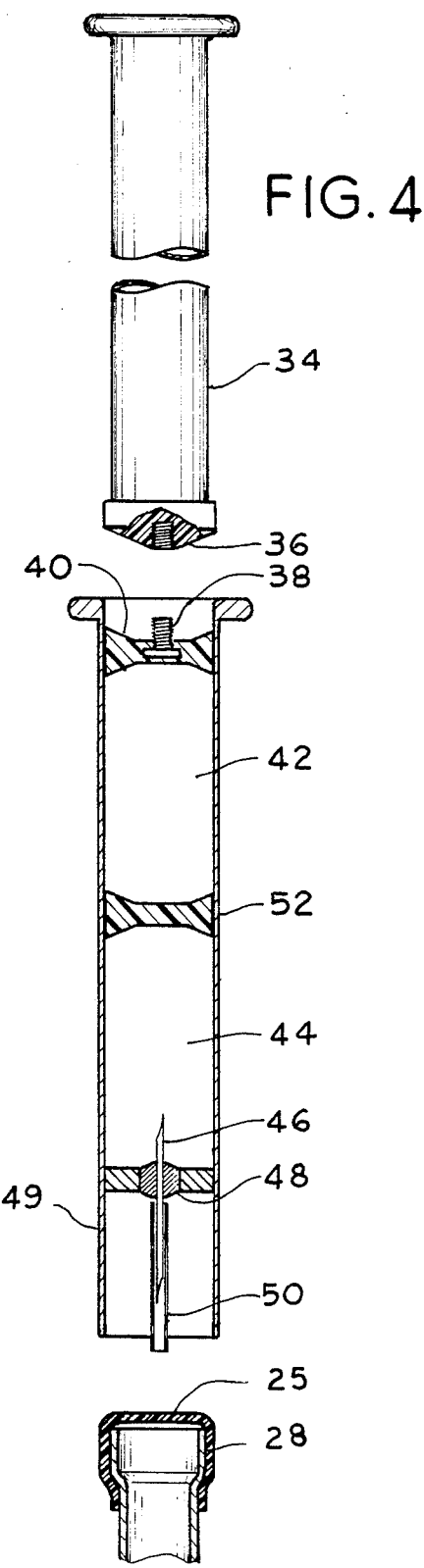

INTRAVENOUS PORT INJECTION AND CONNECTOR SYSTEM

BACKGROUND OF THE INVENTION

Retractable safety needles have been described in our prior U.S. Pat. No. 4,676,783, issued June 30, 1987. These needles prevent needlestick injury for intravenous (IV) needles which are used to administer medication or other fluids into a patient's veins.

Other types of needles pose serious health risks to health care workers who are required to handle them.

U.S. Pat. No. 4,606,734 shows an outer tubular member 23 having flanges 29, 39.

U.S. Pat. No. 4,294,249 shows the basic "Y" connection for intravenous lines.

U.S. Pat. No. 3,474,351 shows a sheath 10 used for connecting a vial.

Needlestick injury is also a threat during heparin IV injections, particularly because of the number of times the needles have to be handled, assembled and disassembled. Some references that may be relevant are as follows:

U.S. Pat. No. 4,592,745 shows a dispenser having two body sections and a plunger.

U.S. Pat. No. 4,281,653 shows a screw-in plunger 5.

U.S. Pat. No. 4,116,196 shows a needle having inner and outer points and a plunger that moves a body of fluid toward the the inner point and diaphragm 24.

U.S. Pat. No. 4,439,184 shows a two-dose syringe in which a plunger-driven piston 26 forces fluid from two chambers through a cannula, but not a needle. The device is intended for urethral catheterization.

U.S. Pat. No. 4,044,758 shows a two-compartment syringe with a needle 56 used to puncture a membrane separating the tubes. The liquids are an irrigation liquid and a contrast medium.

Unintentional needlestick injuries are extremely common in health care workers (nurses, physicians, laboratory workers, housekeeping personnel, etc.). Needlestick exposures can result in transmission of hepatitis B, non A non B hepatitis, and potentially, the acquired immunodeficiency syndrome (AIDS) or other transmissible diseases. Needlestick injuries are a greater risk for health care workers in the 1980's than ever before. Furthermore, each reported needlestick injury costs the health care provider time and money.

Unintentional needlestick injuries can occur when doctors, nurses, I.V. technicians or other hospital workers impale themselves on needles used to connect an auxiliary intravenous line (I.V.) to an auxiliary port on the primary I.V. line. The needlesticks occur when the auxiliary I.V. line inadvertently pulls apart from the primary I.V. line and the health care worker is stuck by the exposed needle dangling at the end of the auxiliary line. The problem is three-fold. First, a common, unprotected hypodermic needle is used to join the two I.V. lines which, by its design, presents a considerable hazard of needlestick. Second, there is no catching mechanism to keep the two lines firmly attached so inadvertent separation of the two lines is a frequent occurrence with considerable risk of needlestick when the exposed needle dangles at the end of the separated line. Third, disposal is difficult because a sharp needle is left attached to an unwieldy intravenous line. Therefore, a new design for I.V. line connectors is urgently needed to provide protection from exposure to the needle and also to secure the connections between I.V. lines.

A related problem is the risk of needlesticks when injecting medication into an I.V. port. Currently, a common hypodermic needle/syringe assembly is used to draw medication from a vial and inject it into an I.V. port or I.V. catheter port. Health care workers sustain needlestick injuries when they try to recap the hypodermic needle to protect themselves from it or when the device is jostled after use or by other accidental means. A safety design is urgently needed for needles used to inject medications into I.V. ports or I.V. catheter ports, to protect health care workers from the danger of these exposed, contaminated needles.

The heparin flush is a special case of hazard of needlestick when injecting into I.V. ports. The current heparin flush procedure requires a succession of three syringes, one to inject the medication, a second to inject a saline solution, and a third to inject a heparin solution. The procedure produces three exposed hypodermic needles that must be carefully disposed of. Because of the extensive handling of needles, the risks of needlestick are very high during and after this procedure. Furthermore, in most hospitals, the syringes used for the saline and heparin solutions must be assembled before use and disassembled after use, which greatly increases the hazard of needlestick and also is awkward and inconvenient for the employee performing the procedure. Therefore, safety improvements for the heparin flush are urgently needed to reduce the exposure of health care workers to exposed needles, to eliminate the need to manually disassemble a contaminated item, and to simplify the handling of needled devices while performing this procedure.

SUMMARY OF THE INVENTION

To solve the aforementioned problems, we have developed a safety connector for auxiliary I.V. lines which shields the connector needle so that it is never exposed to health care workers, and that also provides a clasp mechanism to prevent the inadvertent detachment of the two I.V. lines. The safety connector has an adapter hub which attaches to the end of the auxiliary line by friction fit. A needle protrudes outward from the hub and is long enough to pierce the rubber septum of the primary I.V. line port. A protective collar also extends outward from the needle hub. It extends beyond the length of the needle and has a diameter slightly greater than that of the connecting I.V. port. The collar provides a barrier between the needle and the hands of the health care worker. In open position, an external ring rests near the hub end of the connector and the protective collar is slightly open at the distal end allowing for ease of connection with the I.V. port. When the connector needle is in place well within the I.V. port, the external ring is pushed downward to closed position. This forces the protective collar to close firmly around the I.V. port. It is configured such that internal gripping means engage the I.V. port at its narrowest point to preclude the connector from slipping past the wider end of the port. To disconnect the connector, the external ring must be pushed back to open position, releasing the gripping means from the I.V. port and allowing removal of the needle. A second embodiment involves direct gripping of the I.V. port by the connector via friction without an external ring.

Currently, when syringes are used to inject medication into I.V. ports, a separable hypodermic needle is attached to the syringe. This is the same needle/syringe assembly used for hypodermic injections. The shape of an intravenous port, however, allows for a needle design that protects the hands of health care workers from exposed needles. The needle in FIG. 3 attaches to the end of a syringe by friction fit. The needle protrudes outward from the hub and is long enough to pierce the rubber septum of an I.V. port. A protective collar also extends outward from the hub and extends beyond the length of the needle and has a diameter of slightly greater than that of the I.V. port. The collar provides a permanent barrier between the hands of the health care worker and the contaminated needle. A second embodiment provides for a slot in the collar as a means for clearly viewing the needle. The assembly would optimally include modification of the shape of a medication vial stopper to resemble and I.V. port configuration (FIG. 3). Medication could then be drawn into the syringe using the safety needle and injected into the I.V. port using the same needle.

We have developed a safety heparin flush system that reduces the risk of needlestick injury by providing a barrier between contaminated needles and the hands of health care workers (FIG. 4). It also eliminates one needle/syringe assembly from the current procedure, eliminates the need to assemble and disassemble the required needled devices, and greatly improves the convenience of carrying out the procedure. The described system would be used after medication is injected into an I.V. port.

The heparin flush is a standard procedure in medical practice and is routinely performed following the injection of medication into an access port on an intravenous line. The purpose of the heparin flush is to push the medication through the short length of intravenous tubing into the patient to assure that the full dose of medication has reached the patient's circulation. The heparin solution also keeps the intravenous access route open by preventing blood from coagulating within the intravenous catheter. There is a standard method for performing the heparin flush which is both hazardous and inconvenient. The current method will first be described, followed by the proposed method designed to overcome both the hazards and inconvenience of the current method.

Currently, medication is drawn into a standard syringe, and injected into the patient's intravenous port. The used syringe is set aside. Then a needle/cartridge assembly prefilled with a saline solution is loaded into a reusable syringe holder, and the saline is injected into the intravenous port, pushing the medication into the patient. The spent needle/cartridge assembly is removed from the reusable holder. This is hazardous because the health care worker must manipulate the exposed, contaminated needle, or recap the needle, which is against the accepted safety guidelines proposed by the National Centers of Disease Control. The spent cartridge is commonly placed near the used syringe. Next, a needle/cartridge assembly prefilled with a heparin solution is loaded into the reusable syringe holder, and the heparin is injected into the intravenous port to keep the port from becoming clogged with the patient's blood. Again, the disposable needle/cartridge must be removed from the holder, and set aside with the other two contaminated devices. Usually, the three used devices are disposed of after the procedure is complete. The health care worker must either carry three uncapped needle devices to a disposal container, or put themselves at risk by attempting to recap the needles before disposal. The saline and heparin may also be drawn into standard disposable syringes for the procedure. This method would also produce three exposed needles for disposal.

The new heparin flush safety system applies to the administration of the saline and heparin solutions. As above, medication is drawn into a standard syringe, and injected into the patient's intravenous port. The used syringe is set aside. With the new method, the saline and heparin solutions, contained in the same disposable syringe, are then injected into the intravenous port with a single push of the plunger. The two solutions, separated by a rubber septum, are accessed sequentially by an inner needle. The outer needle is recessed within a collar that has a diameter slightly greater than the intravenous port. Thus, the heparin flush is accomplished in a single motion, one syringe is eliminated from the procedure, and the hands of the health care worker are automatically protected from the needle which is recessed within the collar. The preferred embodiment also includes the use of a needle recessed within a protective collar for the initial syringe (medication), and would require medication vials to have the same configuration as intravenous ports. In that case, both the medication and heparin flush syringes would provide automatic protection from exposed needles. The syringes may then be disposed of without risk to health care workers. The time required for this simplified method would be much less than for the current method.

In the new system, a saline solution and a heparin solution are prepackaged in a single syringe. The two solutions are separated by a rubber septum. The syringe contents are contained in a closed system. The distal end is closed by a rubber stopper and the proximal end is closed at the syringe base and by a rubber sleeve closing off the needled end. A second embodiment is the replacement of the removable rubber sleeve by a plastic cap at the proximal end. To use, the plunger is attached to the rubber stopper by screwing them together. The rubber sleeve or proximal plastic cap is removed from the outer needle. The outer needle is inserted into the I.V. port and the protective collar advances around the outside of the I.V. port. Then forward pressure is applied to the plunger which forces the saline solution into the I.V. port. When the saline solution has been emptied into the I.V. port, the inner needle pierces the rubber septum and accesses the heparin solution which is then forced into the I.V. port as forward pressure continues to advance the plunger. When the entire syringe contents have been emptied, the needle is withdrawn from the I.V. port. The protective collar that extends beyond the length of the needle provides a barrier between the contaminated needle and the hands of health care workers and provides protection from inadvertent needlestick injuries. After use, the plunger can be unscrewed from the rubber stopper of the syringe. The empty syringe barrel is disposable, while the plunger is reusable without limit. A second embodiment includes the plunger and rubber stopper as a single unit, to be disposed of with the syringe.

The apparatus solves the heparin flush problem by taking a multi-step procedure which results in two exposed needles, reducing it to a one-step procedure resulting in no exposed needles. This method adds not only safety but considerable convenience, as well, and should be less expensive.

BRIEF DESCRIPTION OF THE DRAWINGS

FIG. 1 is a side elevation of one embodiment of the invention.

FIG. 1A is a side elevation view of the connector shown in isolation from other structure in a pre-attachment mode.

FIG. 2 is a cross-sectional view of the embodiment of FIG. 1.

FIG. 2A is a side elevation of the connector shown in the locked position and shown in isolation from other structure.

FIG. 3 is a side elevation view of another embodiment of the invention.

FIG. 4 is a side elevation, partly in section, of another embodiment of the invention.

DETAILED DESCRIPTION OF THE DRAWINGS

A safety connector system for auxiliary intravenous lines is generally referred to by the numeral 1 in FIG. 1. The system is based on a connector 2 which is shown in various views and modes of operation in FIGS. 1, 1A, 2 and 2A. The connector 2 is preferably made of a resilient or elastomeric or otherwise flexible material and many different plastic materials may be suitable. Also, the connector could be made of natural or synthetic rubber.

The connector has an upper portion 4 and a lower cylindrical portion 6 which is longitudinally split to provide expandable sections 8, 9.

The upper portion 4 has a cavity 12 adapted in shape to receive and hold, by interference fit, a line adapter hub 14.

The interior of the lower portion 6 is adapted in shape to provide an inner lip 15 which is used to grip a headed portion 16 of an intravenous line.

The connector is intended to be used to connect a standard auxiliary line with hub 14 to I.V. line 18 through a standard Y-joint 19 having branch 20 and line 22.

The auxiliary branch 23 provides an intravenous line port 25 which provides the entrance for needle 26, which pierces membrane 25. Membrane 25 is preferably a rubber septum held over the port by a band of shrink-wrap material shown in FIG. 2 as a heavy black line.

The needle 26 is fixed in position in the connector 2 at 27. By fixing the needle in the connector, instead of on the end of hub 14, the point of the needle is always shielded from health care workers by the lower portion 6 of the connector and, to a certain extent, the upper portion of the connector 4.

After the adaptor hub 14 is inserted into the cavity 12 of the connector, the connector is placed over the end of headed portion 16, initially with ring 9 in an uppermost or open position in which the ring 9 abuts an upper lip 11 which restricts upper movement of the ring 10 beyond a certain point. After the connector is pushed downwardly, with the needle 26 piercing the membrane 25, and after positioning the inner shoulder 15 over the bottom of the headed portion 16, the ring 9 is slid downwardly towards the bottom of the connector to effectively close the gap between portion 8 and portion 9 of the connector. In so doing, a tight connection is made between the headed portion and the connector, thereby holding the needle firmly in place. Separation cannot occur without first moving the ring 9 upwardly. In the downwardmost position of the ring 9, the ring will abut another lip which prevents further downward movement of the ring.

It is possible to connect the connector to the headed portion before the hub is inserted into the cavity 12 of the connector. In either case, there is no possibility for a health care worker to be accidentally stuck by the needle 26.

A variation, with slight modification, is shown in FIG. 3 in which the connector 2 is adapted to receive a syringe in cavity 12. This embodiment is more specifically adapted for the use of a standard syringe which is used to draw medicine from a medication vial or to inject medication into a standard intravenous port. In this embodiment, the needle 26 is not required to be in a fixed position for an extended period of time and therefore, the sliding collar and inner shoulder are not necessarily required, although they could be provided.

In the embodiment of FIG. 3, a standard intravenous port 30 is shown prior to piercing of the membrane 32 with needle 26. As a slight but effective variation on the other embodiment, a gap 29 is provided as a viewing slot so that the health care worker can aim the needle 26 as it is pushed through the membrane 32. The gap 29 may be on one side or it may be on diametrically opposite sides of the connector as shown in FIG. 3. The gap is needed if the needle 26 is otherwise obscured from vision by the connector 2. However, it is conceivable that the connector 2 could be made of a transparent plastic material which would enable the health care worker to view the needle.

Also shown in FIG. 3 is the upper portion of a medicine bottle which has been modified to resemble the intravenous port configuration. This would facilitate use of the connector 2 which has been designed to receive the intravenous port.

In FIG. 3, a needle hub is received in the cavity 12 in a tight interference fit, as is done in the embodiment of FIG. 1.

In the embodiment of FIG. 4, a safety heparin flush system is disclosed in which a plunger 34 is provided with a rubber tip 36 and a threaded bore for receiving a screw 38 provided in a rubber stopper 40.

A rubber septum divides the cylinder into two compartments 42, 44, with compartment 42 designed to contain a heparin solution and compartment 44 designed to contain a saline solution. A fixed closed end 48 is provided in the syringe and holds needle 46 in place as shown.

Needle 46 is double pointed, with a lower portion of the needle and the lower point being covered by sheath 50. In use, the sheath 50 is removed and the plunger 34 is attached while the headed intravenous port is introduced into an open end of the syringe.

A lower end portion 49 surrounds the outer needle portion of the needle 46 so as to protect the health care worker from accidental needlestick injury.

When the plunger is pushed into the syringe, fluid pressure causes the intermediate piston 52 to move downwardly and thereby cause the expulsion of the contents of chamber 44. Eventually, the intermediate piston 52, which is preferably made of rubber or a rubber-like material, will be forced onto the inner needle portion of the needle 46, whereby the inner needle point punctures the intermediate piston. Further downward movement of the plunger will cause the contents of chamber 42 to be expelled in a similar fashion.

Each embodiment described herein uses a portion of a body member to house and enclose a needle, and particularly the point of the needle. Therefore, it should be understood that the needles disclosed herein are not intended to be used to stick into the body of a patient, but are instead intended to be used in intravenous ports or medication vials and similar structures where the cylindrical housing of the needle is slid over the cylindrical end of an intravenous port, with the needle disposed within the housing so as to avoid possible needlestick injury.

We claim:

1. A safety heparin flush apparatus comprising:
   a syringe having a cavity at one end for receiving a headed portion of an intravenous line port and having a fixed closed end forming an end of the cavity,
   a double pointed needle mounted centrally in the fixed closed end of the syringe and having an outer needle portion extending towards an open end of the cavity of the syringe and an inner needle portion extending towards a top end of the syringe, wherein the entire outer needle portion is within the cavity of the syringe in order to prevent needle injuries,
   an upper piston normally disposed near the top end of the syringe,
   a plunger connectable or connected to the piston to impart downward movement of the piston,
   at least one intermediate piston disposed in the syringe between the upper piston and the fixed closed end of the syringe, the syringe containing saline solution in a chamber defined by the fixed closed end of the syringe and the intermediate piston and heparin solution in a chamber defined by the intermediate piston and the upper piston, wherein the intermediate piston prevents the mixing of the solutions within the syringe,
   whereby downward movement of the plunger imparts downward movement of the intermediate piston and causes expulsion of the saline solution through the needle until the needle pierces the intermediate piston, whereby further downward movement causes expulsion of the heparin solution.

2. The apparatus of claim 1 further comprising a removable sleeve which is placed over the outer needle portion prior to use.

3. The apparatus of claim 1 wherein the upper and intermediate pistons are made of rubber or rubber-like material.

4. The apparatus of claim 1 wherein the upper piston is provided with an upwardly extending screw for connecting the upper piston to a rubber tip of the plunger.

5. The apparatus of claim 4, wherein the rubber tip of the plunger is provided with a downward extending threaded bore for receiving the upwardly extending screw of the upper piston.

6. A heparin flush method comprising,
   packing a saline solution and a heparin solution separately in a single syringe wherein the two solutions are separated by a rubber septum,
   attaching a plunger to a stopper disposed at one end of the syringe,
   inserting a needle disposed at the opposite end of the syringe into an I.V. port, wherein the entire needle is within a protective collar which, after insertion, engages an outside of the I.V. port,
   applying forward pressure to the plunger thereby forcing saline solution into the I.V. port until the saline solution is exhausted,
   applying further forward pressure, thereby forcing the needle through the rubber septum to expel the heparin solution into the I.V. port until the heparin solution is exhausted,
   withdrawing the needle from the I.V. port.

* * * * *